United States Patent [19]
Kinomura et al.

[11] Patent Number: 4,874,852
[45] Date of Patent: Oct. 17, 1989

[54] GLYCOSIDATION CATALUST AND PROCESS FOR PREPARING GLYCOSIDE DERIVATIVES

[75] Inventors: Keisuke Kinomura, Kakogawa; Sadaya Kitazawa, Himeji; Yasushi Takata; Toshiyuki Sakakibara, both of Kobe, all of Japan

[73] Assignee: Nippon Fine Chemical Co., Ltd., Osaka, Japan

[21] Appl. No.: 321,809

[22] Filed: Mar. 10, 1989

Related U.S. Application Data

[62] Division of Ser. No. 101,458, Sep. 28, 1987.

[30] Foreign Application Priority Data

Sep. 29, 1986 [JP] Japan ............................ 61-230485
Dec. 22, 1986 [JP] Japan ............................ 61-307434

[51] Int. Cl.4 .................. C07G 3/00; C07G 17/00; C07H 15/04; B01J 27/14
[52] U.S. Cl. .................. 536/18.6; 536/18.5; 536/124; 536/120; 502/208; 502/209; 502/210; 502/211
[58] Field of Search .............. 536/120, 121, 17.1, 536/4.1, 18.5, 18.6, 124; 502/209, 210, 211

[56] References Cited

U.S. PATENT DOCUMENTS 2,390,507 12/1945 Cantor .......................... 536/4.1
3,201,385  8/1965 Jarrett .......................... 536/18.5
3,296,245  1/1967 Kaiser et al. .................. 536/18.6
3,375,243  3/1968 Nevin et al. ................... 536/18.6
3,598,865  8/1971 Lew ............................. 536/4.1
3,707,535 12/1972 Lew ............................. 536/4.1
3,772,269 11/1973 Lew ............................. 536/18.6

OTHER PUBLICATIONS

J. Am. Chem. Soc. (vol. 74), by J. E. Odotte, F. Smith & D. Spriestersbach, Mar. 20, 1952, pp. 1501–1504.
Tetrahedron, 1967, vol. 23, pp. 693–707, Pergamon Press Ltd., A New Method of Glycosylatin.
Tetrahedron Letters No. 9, pp. 657–660, 1976, Pergamon Press Chemistry of the Glycosidic Linkage, Lewis Actid Catalyzed Glycosidation with Amide Acetals and Lactim Ethers.
Journal of the America Chemical Society, 97:14, Jul. 9, 1975 pp. 4056–4062 Halide Ion Catalyzed Glycosildatio Reactions Syntheses of—Linked Disaccharides.
Chem. Pharm. Bull., vol. 24, 1976, pp. 394–399, A facile O-Glycosidation using Stannic Chloride.
Can. Journal of Chemistry, vol. 57, 1979, pp. 2085–2089, Tannic Tetrachloride Catalysed Glycosylation of 8-ethoxycarbonyloctanol by Cellobiose, Lactose, and Maltose Octaacetates; synthesis of $\alpha$- and $\beta$-Glycosidic Linkage.
Can. Journal of Chemistry, vol. 57, pp. 2091–2097, 1,2-Orthoacetate Intermediates in Silver Trigluoromethanesulphonate promoted Koenigs–Knorr Synthesis of Disaccharide Glycosides.

Primary Examiner—Ronald W. Griffin
Assistant Examiner—E. White
Attorney, Agent, or Firm—Armstrong, Nikaido, Marmelstein, Kubovcik & Murray

[57] ABSTRACT

Disclosed are a glycosidation catalyst comprising at least one of heteropoly acids represented by the formula

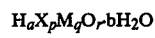

$H_aX_pM_qO_r \cdot bH_2O$ wherein X is P, As, Si or Ge, M is at least one species selected from the group consisting of Mo, W and V, a is 3 4 or 6, b is an integer of 0 to 30, p is 1 or 2, q is 12 or 18, and r is 40 or 62, with the proviso that when X is P or As, a is 3 or 6; when X is Si or Ge, a is 4; and further (1) when X is P or As and a is 3, or when X is Si or Ge and a is 4, M is at least one species selected from the group consisting of Mo, W and V, p is 1, q is 12 and r is 40; and (2) when X is P or As and a is 6, M is Mo or W, p is 2, q is 18 and r is 62, and a process for preparing a glycoside derivative by using said catalyst.

8 Claims, No Drawings

GLYCOSIDATION CATALUST AND PROCESS FOR PREPARING GLYCOSIDE DERIVATIVES

This is a division of application Ser. No.101,458 filed Sep. 28, 1987.

The present invention relates to a catalyst for preparing glycoside derivatives and to a process for preparing glycoside derivatives by using the catalyst.

It is well known that monosaccharides, oligosaccharides or polysaccharides, i.e. condensation products of monosaccharides, play an important role in transmission of information in the living body. To elucidate the mechanism of saccharides for this function, various glycoside derivatives have been prepared by the reaction for conversion of saccharide compounds to glycoside derivatives. Of glycoside derivatives, those which are bio-degradable or unlikely to irritate the skin or eyes are drawing attention for its use as a surfactant. Glycosidation of a saccharide useful as a pharmaceutical gives advantages to the resulting glycoside such as reduced sensitization properties and higher in vivo absorbability.

The glycosidation reaction in which a glycoside linkage is introduced into the saccharide compound by substitution includes, for example, reaction for conversion to O-glycoside, reaction for conversion to S-glycoside, aglycone-exchange reaction and the like.

Various glycosidation reactions have been heretofore proposed. For example, according to the Koenigs-Knorr method for conversion to O-glycoside, a glycoside is produced by acylating and halogenating a saccharide and reacting the acetohalogenated saccharide with an alcohol in the presence of an acid scavenger. However, this method has drawbacks. For example, the method requires a halogenation step which is indispensable; the acetohalogenated saccharide is instable and prone to decomposition; and the method employs an equimolar or more amount of an acid scavenger such as $Ag_2O$, $AgCO_3$ or like silver salts which are expensive, or $HgO$, $Hg(CN)_2$, $CdCO_3$ or like heavy metals which are difficult t dispose of.

In the Helferich method, a glycoside is prepared by acylating a saccharide and reacting the acylated saccharide with an alcohol in the presence of a catalyst such as p-toluenesulfonic acid, $ZnCl_2$, phosphorus oxychloride or the like. This method, however, is defective in, for example, decomposing the sugar ring, breaking the sugar chain when a disaccharide or higher saccharide is used as a starting material and causing coloration. Further the method provides the desired compound in low yields.

Other methods heretofore proposed include a reaction for conversion to S-glycoside, aglycone-exchange reaction and the like for synthesis of glycoside derivatives. Yet these reactions according to known methods entail the shortcomings of producing the contemplated derivatives in low yields, giving rise to coloration (browning), decomposing the sugar ring and breaking the sugar chain when a disaccharide or higher saccharide is used as a starting material, resulting in production of desired derivative in further lower yields.

In addition, conventional glycosidation methods may fail to synthesize the desired glycoside derivative depending on the kind of starting compounds. Even if the methods manage to synthesize a glycoside derivative, the resulting reaction product may contain not only the desired glycoside derivative but large amounts of by-products such as browned sugar, decomposition products of sugar ring and sugar chain and the like which make it very difficult to separate and purify the desired glycoside derivative.

As described above, conventional glycosidation methods remain to be improved in various respects. The drawbacks of the methods are attributable not only to the physico-chemical characteristics that the starting saccharide compounds have a low solubility in organic solvents, but also to the use of conventional catalyst which is responsible for one or more of the following disadvantages depending on the kind of glycosidation reaction using the catalyst: (1) the sugar chain breaks and the sugar ring decomposes, (2) when a plurality of reactive functional groups are present, it is significantly difficult to determine the position of functional group participating in the reaction and stepwise introduction of protective group is required for this determination, necessitating a multistage modifying reaction, (3) a stereospecific reaction is difficult to effect and a stereoisomer of desired compound is provided as a by-product, and (4) a number of side reactions tend to occur and browning, characteristic of sugar reaction, is likely to take place.

It is an object of the present invention to provide a novel catalyst which is capable of producing a glycoside derivative at a high selectivity and in a high yield free of the drawbacks of conventional catalysts in preparation of glycoside derivative by modifying a saccharide compound It is another object of the invention to provide a process capable of producing the contemplated glycoside derivative at a high selectivity and in a high yield.

These and other objects of the present invention will become apparent from the following description.

The objects of the invention can be fulfilled by a catalyst for use in conversion of a saccharide compound, i.e. saccharide or O-glycoside, to a glycoside derivative, the catalyst comprising at least one of heteropoly acids represented by the formula $$H_aX_pM_qO_r \cdot bH_2O \tag{1}$$

wherein X is P, As, Si or Ge, M is at least one species selected from the group consisting of Mo, W and V, a is 3 4 or 6, b is an integer of 0 to 30, p is 1 or 2, q is 12 or 18, and r is 40 or 62, with the proviso that when X is P or As, a is 3 or 6; when X is Si or Ge, a is 4; and further (1) when X is P or As and a is 3, or when X is Si or Ge and a is 4, M is at least one species selected from the group consisting of Mo, W and V, p is 1, q is 12 and r is 40; and (2) when X is P or As and a is 6, M is Mo or W, p is 2, q is 18 and r is 62.

Our research reveals that the heteropoly acids represented by the formula (1) exhibit a remarkable catalytic effect in the glycosidation reaction, so that even if a saccharide compound used as a starting material is a disaccharide or higher saccharide to say nothing of monosaccharide, the desired glycoside derivative can be obtained at a high selectivity and in a high yield without decomposition of sugar ring, breakage of sugar chain nor coloration by browning. Our further discovery was that when the heteropoly acid is used as a catalyst in the glycosidation reaction, the reaction proceeds irrespective of the kind of starting compounds and assures the production of desired glycoside derivative in a high yield and that because of no formation of by-product, the glycoside derivative obtained can be easily separated and purified. Moreover, the catalyst has the additional advantage that the anomer ratio of glycoside derivative obtained can be adjusted as desired by varying the level of reaction pressure or the kind of heteropoly acid.

The heteropoly acids of the formula (1) to be used as the catalyst in the present invention include the heteropoly acids of Keggin structure represented by the formula (1a) and heteropoly acids of Dawson structure represented by the formula (1b).

$$H_{a'}XM_{12}O_{40} \cdot bH_2O \tag{1a}$$

wherein X, M and b are as defined above, and a' is 3 or 4 with the proviso that when X is P or As, a' is 3 and that when X is Si or Ge, a' is 4.

$$H_6X'_2M'_{18}O_{62} \cdot bH_2O \tag{1b}$$

wherein b is as defined above, x' ia P or As and M' is Mo or W.

preferred examples of the heteropoly acids of the formula (1a) or (1b) are phosphotungstic acid ($H_3PW_{12}O_{40} \cdot bH_2O$ or $H_6P_2W_{18}O_{62} \cdot gH_2O$), phosphomolybdic acid ($H_3PMo_{12}O_{40} \cdot bH_2O$ or $H_6P_2Mo_{18}O_{62} \cdot bH_2O$), phosphovanadic acid ($H_3PV_{12}O_{40} \cdot bH_2O$), silicotungstic acid ($H_4SiW_{12}O_{40} \cdot bH_2O$), silicomolybdic acid ($H_4SiMo_{12}O_{40} \cdot bH_2O$), silicovanadic acid ($H_4SiV_{12}O_{40} \cdot bH_2O$), arsenotungstic acid ($H_3AsW_{12}O_{40} \cdot bH_2O$ or $H_6As_2W_{18}O_{62} \cdot bH_2O$), arsenomolybdic acid ($H_3AsMo_{12}O_{40} \cdot bH_2O$ or $H_6As_2Mo_{18}O_{62} \cdot bH_2O$), arsenovanadic acid ($H_3AsV_{12}O_{40} \cdot bH_2O$), germanotungstic acid ($H_4GeW_{12}O_{40} \cdot bH_2O$), germanomolybdic acid ($H_4GeMo_{12}O_{40} \cdot bH_2O$, germanovanadic acid ($H_4GeV_{12}O_{40} \cdot bH_2O$), phosphovanadotungstic acid ($H_3PV_2W_{10}O_{40} \cdot bH_2O$), phosphovanadomolybdic acid ($H_3PV_2Mo_{10}O_{40} \cdot bH_2O$), phosphomolybdotungstic acid ($H_3PMo_6W_6O_{40} \cdot bH_2O$), etc.

While any of the heteropoly acids exemplified above are usable in the present invention, the heteropoly acids of the formula (1a) having a Keggin structure are preferred in view of the stability of catalyst. Among them, most preferable are 12-tungstophosphoric acid, 12-molybdophosphoric acid, 12-tungstosilicic acid, 12molybdosilicic acid, 12-vanadophosphoric acid, 12vanadosilicic acid, etc.

These heteropoly acids are usable singly or at least two of them can be used in mixture. Such heteropoly acids may be supported by silica gel, alumina, activated carbon or like carrier for use as an insoluble catalyst. The heteropoly acid can be supported by a carrier according to conventional methods, e.g. by adding a carrier to a solution of a heteropoly acid, fully mixing the mixture and drying the same under reduced pressure. The amount of heteropoly acid supported by the carrier is not specifically limited but usually about 5 to about 50% by weight, based on the weight of the carrier. Further the heteropoly acids can be used in mixture with a conventional catalyst such as $ZnCl_2$, p-toluenesulfonic acid or the like.

Our continued research revealed that when combined with a specific kind of metal salt, the heteropoly acid can exhibit a higher catalytic activity, leading to the production of contemplated glycoside derivative in higher yields. Examples of useful metal salts are inorganic acid salts or organic acid salts of metals pertaining to the Group II, IV or VIII of the periodic table, alkali metals or like metals. Preferred examples thereof are acetates or sulfates of Zn, Sn, Co, Cs, Ce, Ni, Sr or like metals, carbonates of Li, K, Na or like metals, etc. The amount of metal salt to be combined with the heteropoly acid is about 2 to about 50% by weight, preferably about 5 to about 30% by weight, based on the heteropoly acid.

The catalyst of the invention comprising the heteropoly acid or a combination of heteropoly acid and metal salt has a remarkable catalytic activity in the glycosidation reaction by replacement of group with another to introduce a glycoside linkage into the saccharide compound. Examples of such glycosidation reactions are reactions for conversion to O-glycoside, reactions for conversion to S-glycoside, aglycone-exchange reactions and the like. The reactions give at a high selectivity and in a high yield the contemplated glycoside derivative such as alkylglycoside, arylglycoside or like O-glycoside, alkylthioglycoside, arylthioglycoside or like S-glycoside, oligosaccharide or the like.

Typical reactions are discussed below to clarify the present invention.

(a) Reaction for conversion to O-glycoside and reaction for conversion to S-glycoside The reaction is carried out by reacting the acylated saccharide with a saccharide having one or more unprotected OH groups or with a compound represented by the following formula (2) in the presence of the heteropoly acid or a combination of heteropoly acid and metal salt as a catalyst $$R_1—AH \tag{2}$$

wherein $R_1$ is hydrocarbon group optionally having at least one substituent and A is oxygen atom or sulfur atom. By the reaction the hydroxyl group at the 1-position of the saccharide is selectively replaced by $R_1A$-group, wherein $R_1$ and A are as defined above, whereby the desired O-glycoside or S-glycoside is obtained.

Saccharide to be used as a starting compound in the reaction can be any of those heretofore known, such as monosaccharides, polysaccharides, oligosaccharides and the like. Examples of typical monosaccharides are glucose, mannose, galactose, glucosamine, mannosamine, galactosamine and like hexoses, arabinose, xylose, ribose and like pentoses, etc. Examples of representative oligosaccharides are sucrose, lactose, trehalose, maltose, cellobiose, isomaltose, gentiobiose, laminaribiose, chitobiose, xylobiose, mannobiose, sophorose, maltotriose, maltotetraose, and hydrolyzates of starch, cellulose and the like. Examples of typical polysaccharides are chitin, chitosan, starch, cellulose, etc.

Preferable of these saccharides used in the reaction are glucose, galactose, mannose, glucosamine, ribose, arabinose, maltose, cellobiose, maltotriose, chitobiose, etc.

According to the present invention, the saccharide is acylated first. The acylation can be conducted by known methods such as the method of E. Fisher [Chem., Ber., 49, 584 (1916)]. For example, a glucose is acetylated by mixing fine powder of anhydrous glucose with anhydrous sodium acetate and heating the mixture with stirring.

The reaction is conducted by converting the acylated saccharide to a glycoside derivative using a saccharide with one or more unprotected hydroxyl groups or the compound of the formula (2). Examples of saccharide to be reacted with the acylated saccharide include the above-mentioned examples of conventional saccharides useful as the starting compound which, in this application, can be used as they are or with one or more hydroxyl groups left unprotected. The introduction of protective groups can be performed by any of conventional methods, for example, by causing an acetic anhydride and sodium acetate to act on a glucose for acetylation, or by boiling a glucose in a hydrochloric acid gas-containing anhydrous methanol. Exemplary of protective groups to be introduced are acetyl, benzoyl, carbamoyl and like acyl groups, methyl, ethyl, benzyl, silyl, trityl and like alkyl groups, isopropylidene, benzylidene and like cyclic ketals, acetals, etc.

Preferred examples of saccharides used for reaction with the acylated saccharide are glucose, galactose, mannose, glucosamine, ribose, arabinose, maltose, cellobiose, maltotriose, chitobiose, these saccharides partially acylated (e.g., 1,2,3,4-tetra-O-acetyl-D-glucopyranose), these saccharides partially alkylated (e.g., methyl 2,3,4-tri-O-methyl-D-galactopyranoside, benzyl, 4,6-di-O-benzoyl-D-glucopyranoside), etc.

Illustrative of hydrocarbon groups represented by $R_1$ in the compound of the formula (2) are $C_{3\text{-}30}$ hydrocarbon groups such as saturated or unsaturated, straight chain, branched chain or alicyclic hydrocarbon, aromatic hydrocabon and like groups. Exemplary of chain hydrocarbon groups are propyl, isopropyl, butyl, isobutyl, tert-butyl, pentyl, hexyl, octyl, nonyl, decyl, undecyl, dodecyl, tetradecyl, pentadecyl, hexadecyl, heptadecyl, octadecyl, nonadecyl, eicosyl and like straight chain or branched chain alkyl groups, allyl, isopropenyl, 1-propenyl, 1,3-butadienyl, 2-pentene-4-ynyl, 3-methyl-2-butenyl, 9-octadecenyl and like straight chain or branched chain alkenyl groups, benzyl and like aralkyl groups, etc. Representative of alicyclic hydrocarbon groups are cycloalkyl, choresterol residue (monohydric choresterol group from which hydroxyl group has been removed), etc. Representative of aromatic hydrocarbon groups are phenyl, tolyl, xylyl, $\alpha$-naphthyl, $\beta$-naphthyl and like aryl groups, etc. The hydrocarbon groups may have one or more substituents. Typical of substituents for chain hydrocarbon groups are hydroxyl, amino, nitro, chlorine, fluorine, iodine, bromine and like halogen atoms, etc. Illustrative of substituents for alicyclic hydrocarbons or aromatic hydrocarbons are hydroxyl, amino, nitro, chlorine, fluorine, iodine, bromine and like halogen atoms, straight chain or branched chain alkyl groups having approximately 1 to 4 carbon atoms, straight chain or branched chain alkoxy groups having approximately 1 to 4 carbon atoms, hydroxyalkyl, etc.

Examples of the compound of the formula (2) are alcohols, phenols, thiophenols, mercaptans, etc.

Exemplary of alcohols are n-butanyl, eicosanol and like saturated alcohols, allyl alcohol, oleyl alcohol and like unsaturated alcohols, 2-octanol and like secondary alcohols, cholesterol and like sterols, benzyl alcohol and like alcohols with aromatic ring, etc.

Typical of phenols are phenol, hydroquinone, catechol, resorcinol, pyrogllol, phloroglucin, cresol, xylenol, carvacrol, thymol, $\alpha$-naphthol, $\beta$-naphthol, etc.

Representative of thiophenols are the abovementioned examples of phenols with the OH group replaced by SH group. Exemplary of mercaptans are methyl mercaptan, ethyl mercaptan, propyl mercaptan, isopropyl mercaptan, n-butyl mercaptan, allyl mercaptan, lauryl mercaptan and like alkyl mercaptans, benzyl mercaptan and like aralkyl mercaptans, phenyl mercaptan and like aryl mercaptans, etc.

Preferred examples of the compound of the formula (2) are n-butanol, octanol, lauryl alcohol, allyl alcohol, benzyl alcohol, cholesterol, phenol, hydroquinone, $\alpha$-naphthol, nitrophenol, propyl mercaptan, lauryl mercaptan, allyl mercaptan, benzyl mercaptan, phenyl mercaptan, etc.

The conversion to O-glycoside or to S-glycoside is conducted in a manner to be described later. (b) Aglycone exchange reaction The reaction is performed by reacting an O-glycoside with an alcohol or a phenol both represented by the formula $$R_1\text{---OH} \qquad (3)$$

wherein $R_1$ is as defined above in the formula (2) in the presence of a catalyst comprising a heteropoly acid, or a heteropoly acid and a metal salt. The reaction induces replacement of the 1-position group of O-glycoside with $R_1$—O—. 

Oligosaccharides and polysaccharides can be used as they are as O-glycoside in the reaction. Also usable is an O-glycoside prepared by glycosidation of monosaccharides, oligosaccharides or polysaccharides. The O-glycoside can be produced by glycosidation of saccharides by conventional methods or by the methods stated above in (a). Any of saccharides exemplified above for the reaction (a) is also usable as those useful in preparation of O-glycoside. Exemplary of O-glycosides are those with glycoside linkage composed of saccharide and hydrocarbon group such as alkylglycoside, arylglycosides, etc. Exemplary of hydrocarbon groups are propyl, isopropyl, butyl, isobutyl, tert-butyl, pentyl, hexyl, octyl, nonyl, decyl, undecyl, dodecyl, tetradecyl, pentadecyl, hexadecyl, heptadecyl, octadecyl, nonadecyl, eicosyl and like straight chain or branched chain alkyl groups having approximately 1 to 10 carbon atoms, allyl, isopropenyl, 1-propenyl, 1,3-butadienyl, 2-pentene-4-ynyl, 3-methyl-2-butenyl and like straight chain or branched chain alkenyl groups having approximately 1 to 10 carbon atoms, benzyl and like aralkyl groups, cycloalkyl group, phenyl and like aryl groups, etc. The hydrocarbon groups may have one or more substituents. Typical of substituents for alkyl groups, alkenyl groups or aralkyl groups are hydroxyl, amino, nitro, chlorine, fluorine, iodine, bromine and like halogen atoms, etc. Illustrative of substituents for cycloalkyl groups or aryl groups are hydroxyl, amino, nitro, chlorine, fluorine, iodine, bromine and like halogen atoms, straight chain or branched chain alkyl groups having approximately 1 to 4 carbon atoms, straight chain or branched chain alkoxy groups having approximately 1 to 4 carbon atoms, hydroxyalkyl, etc. When required, the hydroxyl group of the glycoside is protected. Exemplary of protective groups and protecting methods are those as described above for the reaction (a). Illustrative of preferred O-glycosides are methyl, tetra-O-acetyl-D-glucoside, benzyl tetra-O-acetyl-D-galactoside, butyl tetra-O-acetyl-D-mannoside, allyl tri-O-acetyl-arabinoside, methyl tetra-O-methyl-glucoside, benzyl tetra-O-benzyl-galactoside, methyl hepta-O-acetyl-maltoside, butyl hepta-O-benzoyl-cellobioside, etc.

The alcohols and phenols of the formula (3) to be used as the reactant can be any of the examples shown above for the reaction (a). In other words, it is suitable to use the alcohols and phenols having the hydrocarbon groups exemplified above as $R_1$ for the reaction (a). Preferred examples of alcohols are butanol, octanol, lauryl alcohol, allyl alcohol, 2-octanol, etc. Preferred examples of phenols are phenol, hydroquinone, α-naphthol, etc.

The reaction (a) and (b) as stated above are effected by reacting the saccharide compound with said reacting compound without a solvent or with a suitable solvent in the presence of a catalyst comprising a heteropoly acid, or a heteropoly acid and a metal salt. The proportions of the saccharide compound and the other reacting compound are not specifically limited and can be suitably determined. Yet it is suitable to use about 1 to about 10 moles, preferably about 1 to about 2.5 moles, of the latter per mole of the former. While not critical, the amount of heteropoly acid is usually about 0.1 to about 5.0% by weight, preferably about 0.5 to about 1.0% by weight, based on the combined amount of saccharide compound and other reacting compound. The reaction is performed at a temperature of about 20° to about 180° C. and is completed in about 1 to about 24 hours.

Examples of suitable solvents are saturated hydrocarbons such as hexane, heptane, octane, ISOPER (trademark, product of ESSO Petroleum Co., Ltd.) and the like; aromatic hydrocarbons such as toluene, xylene, mesitylene, ethyl benzene, lauryl benzene and the like; halogenated hydrocarbons such as chloroform, methylchloroform and the like; ketones such as acetone, diethyl ketone, methyl isobutyl ketone and the like; esters such as ethyl acetate, butyl acetate, ethyl butyrate and the like; and ethers such as diethyl ether, isopropyl ether, ethyelene glycol dialkyl ether and the like.

When the metal salt is used as a catalyst component in said reactions, the metal salt may be added to the reaction system either in mixture with the heteropoly acid or in separate form. The amount of metal salt in either case is not specifically limited but a suitable amount is about 2 to about 50% by weight, preferably about 5 to about 30% by weight, based on the heteropoly acid The glycoside derivative obtained in the reaction (a) or (b) can be separated from the reaction product and purified by conventional purification methods.

The present invention will be described below in greater detail with reference to the following examples and comparison examples.

EXAMPLE 1

(Synthesis of alkylglycoside)

A 0.4 g quantity of phosphomolybdic acid was added to 39 g (0.1 mole) of pentaacetylglucose, 20 ml (0.12 mole) of octyl alcohol and 70 ml of toluene. The mixture was heated to 85° C. with stirring to undergo reaction for 4 hours. The reaction mixture was diluted with ethyl acetate and the dilute was washed with water. The organic layer was concentrated, giving 62 g of pale yellow oil. The oil was purified by silica gel column chromatography using as an eluent toluene-ethyl acetate (4 : 1), giving 32 g of the desired compound, octyl tetra-O-acetyl-$\beta$-D-glucopyranoside, in a yield of about 70%.

COMPARISON EXAMPLE 1

A 0.4 g quantity of p-toluenesulfonic acid was added to 39 g (0.1 mole) of pentaacetylglucose, 20 ml (0.12 mole) of octyl alcohol and 70 ml of toluene. The mixture was heated to 85° C. with stirring to undergo reaction for 4 hours. The reaction mixture was cooled and diluted with ethyl acetate after which the dilute was washed with water. The organic layer was concentrated, producing 62 g of brown oil. The oil contained tetraacetyloctylglycoside, together with a predominant amount of browned starting saccharide. The oil was purified in the same manner as in Example 1, giving only 5 g of the desired compound, octyl tetra-O-acetyl-$\beta$-D-glucopyranoside in a yield of 7.9%.

EXAMPLE 2

(Synthesis of alkylglycoside)

A 0.3 g quantity of phosphomolybdic acid was added to 32 g (0.1 mole) of tetraacetylxylose, 20 ml (0.12 mole) of octyl alcohol and 70 ml of toluene. The mixture was heated to 85° C. with stirring to undergo reaction for 3 hours. The same subsequent procedure as in Example 1 was repeated, producing 32 g of the desired compound, octyl tri-O-acetyl-$\beta$-D-xylofuranoside, as a pale yellow oil in a yield of 82%.

COMPARISON EXAMPLE 2

The same procedure as in Example 2 was repeated with the exception of using 0.3 g of p-toluenesulfonic acid in place of phosphomolybdic acid, giving a product having about 30 mole % of starting saccharide converted to triacetyloctylxyloside and containing large amounts of unreacted portion and decomposed portion of saccharide. The contemplated compound, triacetyloctylxyloside, failed to isolate.

EXAMPLE 3

To 78.0 g (0.20 mole) of pentaacetylglucose were added 57.0 g (0.36 mole) of 1-menthol, 160 ml of toluene and 0.7 g of phosphomolybdic acid. The mixture was reacted at 85° C. for 4 hours. Ethyl acetate (100 ml) was added to the reaction mixture. Thereafter the mixture was washed with water, neutralized and washed again with water. Then the organic layer was concentrated and the residue was recrystallized from an ethanol-water solvent mixture, giving 45.0 g of menthyl tetra-O-acetyl-$\beta$-D-glucopyranoside in a yield of 43%.

COMPARISON EXAMPLE 3

The same procedure as in Example 3 was repeated up to completion of recrystallization with the exception of using 0.5 g of p-toluenesulfonic acid in lieu of phosphomolybdic acid, giving, however, a reaction product consisting of only a portion of starting saccharide and decomposed portion thereof and thus failing to give the desired compound.

EXAMPLE 4

(Synthesis of arylglycoside)

To 39.0 g (0.10 mole) of pentaacetylglucose were added 11.3 g (0.12 mole) of phenol and 0.5 g of phosphomolybdic acid. The mixture was subjected to reaction at 90° C. under reduced pressure of 40 mmHg for 3 hours. Toluene (100 ml) was added to the reaction mixture and the mixture was washed with 2 portions of 0.5M aqueous solution of sodium hydroxide. The organic layer was evaporated to dryness, giving 41 g of pale yellow solid. The solid was recrystallized from ethanol, giving 35.2 g of the desired compound, phenyl 2,3,4,6-tetra-O-acetyl-$\beta$-D-glucopyranoside, in a yield of 83%. M.p. 124 to 125° C., $[\alpha]_D^{21} = -22°$ C. (Cl, CHCl$_3$)

COMPARISON EXAMPLE 4

To 292 g of phenol were added 3.9 g of p-toluenesulfonic acid and 300 g of β-pentaacetyl-D-glucose. The mixture was heated with vigorous agitation in an oil bath for 1.5 hours to undergo reaction. The reaction mixture was extracted with about 400 ml of benzene. The crude product obtained was recrystallized from ethanol, producing solids containing 39 g of the desired compound, phenyl 2,3,4,6-tetra-O-acetyl-β-D-glucopyranoside, in a yield of 42%. The solid thus obtained, which was noticeably colored, was treated with activated carbon for decoloration and recrystallized to form crystals comparable in hue with the compound prepared in Example 4. The crystals obtained weighed 33 g (36% yield).

EXAMPLE 5

(Synthesis of arylglycoside)

To pentaacetylglucose (39.0 g, 0.10 mole) were added 11.3 g (0.12 mole) of phenol and 0.5 g of silicotungstic acid. The mixture was reacted at 90° C. under reduced pressure of 40 mmHg for 3 hours. Toluene (100 ml) was added to the reaction mixture after which the mixture was washed with 2 portions of 0.5 M aqueous solution of sodium hydroxide. The organic layer was evaporated to dryness, giving 45 g of yellow oil. Ethanol was added to the oil and the mixture was left to stand at 0° C. for 24 hours. The precipitated crystals were separated by filtration, giving 30.6 g of the desired compound, phenyl 2,3,4,6-tetra-O-acetyl-α-D-glucopyranoside, in a yield of 72%. M.p. 114° to 115° C.

Examples 4 and 5 show that the anomer ratio of glycoside derivatives obtained varies with the kind of heteropoly acid used.

COMPARISON EXAMPLE 5

To 46 g of phenol were added 12.5 g of zinc chloride and 50 g of β-pentaacetyl-D-glucose. The mixture was heated at 125° to 130° C. with vigorous agitation for 45 minutes. The dark-colored melt obtained with an odor like that of acetic acid was dissolved in 300 ml of benzene. The solution was washed with sodium hydroxide and water several times, dried over calcium chloride, passed through an activated carbon filter, and evaporated to dryness. The residue obtained was recrystallized twice from absolute alcohol, giving 13.3 g of the desired compound, phenyl 2,3,4,6-tetra-O-acetyl-α-D-glucopyranoside, in a yield of 25%.

EXAMPLE 6

(Synthesis of arylglycoside)

To 39.0 g (0.10 mole) of pentaacetylglucose were added 30.0 g (0.15 mole) of hydroquinone monobenzyl ether and 0.5 g of 12-molybdophosphoric acid. The mixture was reacted at 130° C. under reduced pressure of 20 mmHg for 3 hours. Toluene (100 ml) was added to the reaction mixture and the mixture was washed with 3 portions of 50 ml of 0.5M-NaOH aqueous solution at 0° C. The toluene layer was evaporated to dryness after which the residue was recrystallized from ethanol, giving 43.9 g of benzylarbutin tetraaetate in a yield of 83.0%. M.p. 109° to 110° C.

COMPARISON EXAMPLE 6

In 200 ml of dried benzene were dissolved 25 g (0.064 mole) of pentaacetylglucose, 38.4 g (0.192 mole) of hydroquinone monobenzyl ether and 2.5 g of phosphorus oxychloride (containing 1% by weight of water). The solution was refluxed for 3 hours. Although the aglycone was used in a molar ratio twice greater than in Example 6 relative to saccharide, the conversion of contemplated product, benzylarbutin tetraacetate, was not more than 50%. The reaction mixture was washed with 3 portions of 70 ml of 2M-NaOH aqueous solution and with water, but the excess hydroquinone monobenzyl ether failed to migrate to the aqueous phase, making it difficult to separate the desired product from the reaction mixture. After the reaction mixture was left to stand overnight, the benzene layer was dehydrated with calcium chloride and the solvent was distilled off under reduced pressure. The blackish brown oil obtained was recrystallized from ethanol, giving 24.2 g of brown solid containing 13.9 g of benzylarbutin tetraacetate (41%). The solid was recrystallized from ethanol but recrystallization failed to completely remove the hydroquinone monobenzyl ether and to produce the contemplated pure compound.

EXAMPLE 7

To 67.9 g (0.10 mole) of octaacetylmaltose were added 11.3 g of phenol and 0.5 g of 12-molybdophosphoric acid. The mixture was reacted at 100° C. under reduced pressure of 40 mmHg for 3 hours. Toluene (100 ml) was added to the reaction mixture and the mixture was washed with 3 portions of 50 ml of 0.5M-NaOH aqueous solution at 0° C. The toluene layer was evaporated to dryness after which the residue obtained was recrystallized from ethanol, giving 53.4 g of the desired compound, phenyl β-D-maltoside heptoacetate, in a yield of 75%.

COMPARISON EXAMPLE 7

The same reaction as in Example 7 was repeated with the exception of using 0.5 g of p-toluenesulfonic acid in place of 12-molybdophosphoric acid. The reaction product obtained was found, however, to have the sugar chain broken and to be composed predominantly of phenyl β-D-glucopyranoside tetraacetate.

EXAMPLE 8

A 19.5 g (0.05 mole) quantity of penta-O-acetyl-β-D-mannopyranose and 13.9 g (0.10 mole) of p-nitrophenol were heated at 130° C. under reduced pressure of 20 mmHg. To the melt obtained were added 0.25 g of 12-molybdophosphoric acid and 0.05 g of zinc acetate and the mixture was reacted under reduced pressure for 30 minutes. The reaction mixture was dissolved in 100 ml of toluene and the solution was washed with 6 portions of 50 ml of 1.0M-NaOH aqueous solution and with 2 portions of 50 ml of water. After the toluene layer was evaporated to dryness under reduced pressure, the semisolid obtained was purified by silica gel column chromatography using toluene-acetone (20 : 1, v/v) as an eluent, giving 12.2 g of p-nitrophenyl 2,3,4,6-tetra-O-acetyl-β-D-mannopyranoside in a yield of 52.0%. M.p. 142° to 143° C.

EXAMPLE 9

The desired compound (10.1 g) was obtained in a yield of 43.0% by following the same procedure as in Example 8 with the exception of not using zinc acetate.

COMPARISON EXAMPLE 8

The same procedure as in Example 9 was repeated with the exception of using p-toluenesulfonic acid in lieu of 12-molybdophosphoric acid, giving 6.8 g of solid containing 5.6 g of markedly colored contemplated compound. The solid was recrystallized from ethanol to obtain the desired compound comparable in hue with the compound prepared in Example 8. The recrystallization formed 4.9 g of desired compound (21% yield).

EXAMPLE 10

In 100 ml of toluene were dissolved 39.0 g (0.10 mole) of pentaacetylglucose and 16.5 g (0.15 mole) of hydroquinone. To the solution were added 0.5 g of 12-molybdophosphoric acid and 0.1 g of nickel sulfate. The mixture was reacted at 100° C. under atmospheric pressure for 4 hours. The reaction mixture was washed with 2 portions of 50 ml of 0.5M-NaOH aqueous solution after which the toluene was removed under reduced pressure. Ethanol (50 ml) was added to the pale yellow residue obtained, and the mixture was left to stand in a refrigerator for two nights. The precipitated crystals were separated by filtration, giving 28.6 g of 2,3,4,6-tetra-O-acetylarbutin in a yield of 65%. M.p. 136° to 137° C.

EXAMPLE 11

The desired compound (24.2 g) was obtained in a yield of 55% by performing the same procedure as in Example 10 with the exception of not using nickel sulfate.

COMPARISON EXAMPLE 9

The same procedure as in Example 11 was repeated with the exception of using p-toluenesulfonic acid in lieu of 12-molybdophosphoric acid, giving 22.3 g of blackish brown oil containing 18.9 g of desired compound (43% yield). The browned saccharide portion contained in the oil inhibited the crystallization of the desired compound. Ethanol (42 ml) was added to the oil and the mixture was allowed to stand in a refrigerator for 6 months with the result that no crystal was formed.

EXAMPLE 12

(Aglycone exchange)

Phosphomolybdic acid (0.4 g) was added to 35 g (0.1 mole) of methyl 2,3,4,6-tetra-O-acetyl-α-D-glucopyranoside, 20 ml (0.12 mole) of octyl alcohol and 50 ml of toluene. The mixture was heated to 85° C. with stirring under reduced pressure of about 50 mmHg to undergo reaction for 4 hours. The reaction mixture was diluted with ethyl acetate and the dilute was washed with water. The organic layer was concentrated, and the residue obtained was purified by silica gel column chromatography using toluene-ethyl acetate as an eluent, giving 30 g of the desired compound, tetraacetyloctylglucoside, as a pale yellow oil in a yield of 65%.

COMPARISON EXAMPLE 10

The same procedure as in Example 12 was repeated with the exception of using 0.4 g of p-toluenesulfonic acid in lieu of phosphomolybdic acid, giving 18 g of brown oil containing 16.2 g of tetraacetyloctylglycoside (36% yield). The oil was treated with activated carbon for decolorization, giving 15.5 g of tetraacetyloctylglucoside (34% yield) comparable in hue with the oil obtained in Example 12.

EXAMPLE 13

Phosphomolybdic acid (0.35 g) was added to 34 g of octaacetylmaltose, 30 ml of lauryl alcohol and 70 ml of toluene. The mixture was heated to 90° C. with stirring to undergo 4 hours of reaction. The reaction mixture was diluted with ethyl acetate and the dilute was washed with water. The organic layer was concentrated and the residue obtained was purified by silica gel column chromatography, giving 25 g of heptaacetyllaurylmaltoside as a pale yellow oil in a yield of 62%. The other fractions than the desired compound were mainly octaacetylmaltose, i.e. starting compound, but the decomposition product, i.e. the acetylation product of laurylglycoside, was not contained.

COMPARISON EXAMPLE 11

Heptaacetyllaurylmaltoside (2.1 g) was prepared as a pale brown oil in a yield of 5.0 % by repeating the same procedure as in Example 13 with the exception of using 0.34 g of p-toluenesulfonic acid in place of phosphomolybdic acid. A brown oil (10.2 g) containing 5.0 g of an acetylation product of lauryl glycoside and browned saccharide was obtained from the other fractions.

Example 13 and Comparison Example 11 show that the reaction using a heteropoly acid as a catalyst does not cut the saccharide chain.

EXAMPLE 14

(Synthesis of thioglycoside)

A 0.4 g quantity of phosphotungstic acid was added to 39 g (0.1 mole) of pentaacetylglucose, 40 g (0.2 mole) of lauryl mercaptan and 50 ml of toluene. The mixture was reacted in nitrogen atmosphere at 80° C. for 3 hours. The reaction mixture was treated in the same manner as in Example 5, giving 47 g of tetraacetylaurylthioglucoside in a yield of 88%.

COMPARISON EXAMPLE 12

Pentaacetylglucose (39 g, 0.1 mole), 40 g (0.2 mole) of lauryl mercaptan and 50 ml of toluene saturated with hydrogen chloride gas were subjected to reaction in nitrogen atmosphere at 80° C. for 3 hours. The reaction mixture was treated in the same manner as in Example 12, giving 25.1 g of tetraacetyllaurylthioglucoside in a yield of 47%.

EXAMPLE 15

A 78.0 g (0.20 mole) of pentaacetyl β-D-glucopyranose and 49.6 g (0.40 mole) of salicyl alcohol were dissolved in 150 ml of diethylene glycol dibutyl ether. The solution was heated to 100° C. To the solution was added 1.0 g of 12-molybdophosphoric acid. The mixture was reacted at 100° to 110° C. under reduced pressure of 20 mmHg for 2.5 hours while removing the acetic acid produced during the reaction. Ethyl acetate (150 ml) was added to the reaction mixture. Then the mixture was washed with 3 portions of 50 ml of 0.1M-NaOH aqueous solution and 2 portions of 50 ml of water. The organic layer was concentrated under reduced pressure. Hexane was added to the residue after which the precipitated crystals were separated by filtration. The crystals thus obtained were recrystallized from hot ethanol, giving 58.1 g of tetra-O-acetylsalicin in a yield of 64%.

COMPARISON EXAMPLE 13

The same reaction as in Example 15 was repeated with the exception of using 1.0 g of p-toluenesulfonic acid as a catalyst in place of 1.0 g of 12molybdophosphoric acid. A major portion of the resulting reaction product was a mixture of 16.4 g of tetra-O-acetylsalicin (18.0% yield) and 11.63 g of O-hydroxybenzyl-2,3,4,6-tetra-O-acetyl-D-glucopyranoside (12.8% yield). It was impossible to isolate the desired compound, tetra-O-acetylsalicin, as a pure product.

COMPARISON EXAMPLE 14

To 100 ml of dehydrated chloroform were added 13.6 g (0.11 mole) of salicyl alcohol and 25.6 g (0.10 mole) of silver oxide. A solution of 41.0 g (0.10 mole) of acetobromoglucose in 100 ml of chloroform was added dropwise to the mixture with stirring over a period of 1 hour under glare protection. The mixture was further stirred at room temperature for 8 hours after which the solid deposited was filtered off. The filtrate was washed with 2 portions of 100 ml of a 4% sodium hydrogencarbonate solution and with 2 portions of 100 ml of water. The chloroform layer was distilled off under reduced pressure. Ether-petroleum ether was added to the residue to obtain a solid mass. The solid was a mixture of 20.9 g of tetra-O-acetylsalicin (46.0% yield) and 14.3 g of o-hydroxybenzyl-2,3,4,6-tetra-O-acetyl-$\beta$-D-glucopyranoside (31.5% yield). The solid was purified by silica gel column chromatography using as an eluent hexane-ethyl acetate (3 : 2), giving only 14.5 g of the desired compound, tetra-O-acetylsalicin, in a yield of 32%.

EXAMPLE 16

In 80 ml of diethylene glycol dibutyl ether were dissolved 39.0 g (0.10 mole) of pentaacetyl $\beta$-D-glucopyranose and 24.8 g (0.20 mole) of p-hydroxybenzyl alcohol. The solution was heated to 100° C. and 1.0 g of 12-tungstophosphoric acid was added thereto. The mixture was reacted at 100° to 110° C. under reduced pressure of 20 mmHg for 2 hours while removing the acetic acid produced during the reaction. The reaction mixture obtained was treated in the same manner as in Example 15, giving 26.4 g of p-hydroxymethylphenyl 2,3,4,6-tetra-O-acetyl-$\alpha$-D-glucopyranoside in a yield of 58.1%.

COMPARISON EXAMPLE 15

The same reaction as in Example 16 was repeated with the exception of using 5.0 g of $ZnCl_2$ as a catalyst in place of 12-tungstophosphoric acid. The resulting reaction product contained a small amount (5.1 g) of the desired compound, phenylglucoside (11.3% yield) and large amounts of structurally unidentified browned by-products.

EXAMPLE 17

In 170 ml of ISOPER-G (trademark, product of ESSO Petroleum Co., Ltd.) were dissolved 39.0 g (0.10 mole) of pentaacetyl $\beta$-D-galactopyranose and 27.8 g (0.20 mole) of 2-hydroxy-4-methylbenzyl alcohol. The solution was heated to 110° C. To the solution was added 0.7 g of 12-molybdophosphoric acid. The mixture was reacted at 115° C. under reduced pressure of 20 mmHg for 4 hours. Subsequently 100 ml of ethyl acetate was added to the reaction mixture. The mixture was washed with 2 portions of 100 ml of water, followed by removal of the ethyl acetate by distillation under reduced pressure. The residue was left to stand at 0° C. overnight. The precipitated crystals containing an oil were separated by filtration and recrystallized from hot ethanol, giving 23.0 g of 2-hydroxymethyl-5-methylphenyl 2',3',4',6'-tetra-O-acetyl-$\beta$-D-galactopyranoside in a yield of 49.3%.

EXAMPLE 18

(Synthesis of oligosaccharide)

In 200 ml of toluene were dissolved 78 g (0.2 mole) of pentaacetyl-$\beta$-D-glucose and 98 g (0.3 mole) of methyl 2,3,4-tri-O-acetyl-$\alpha$-D-glucopyranose. To the solution was added 1.0 g of 9-molybdo-3-vandophosphoric acid and the mixture was reacted at 100° C. in an atmospheric pressure for 4 hours. The reaction mixture was diluted with 200 ml of toluene after which the dilute was washed with 3 portions of 150 ml of 4% $NaHCO_3$ aqueous solution. The toluene layer was dried over anhydrous magnesium sulfate overnight and concentrated under reduced pressure, giving an oil. The oil was purified by silica gel column chromatography using as an eluent toluene-ethyl acetate (3 : 1), giving 27.3 g of methyl hepta-O-acetyl-D-isomaltoside in a yield of 21%.

COMPARISON EXAMPLE 16

The same reaction as in Example 18 was repeated with the exception of using p-toluenesulfonic acid in place of 9-molybdo-3-vanadophosphoric acid, failing, however, to synthesize the desired compound.

EXAMPLE 19

To 100 ml of methylchloroform were added 19.5 g (0.05 mole) of pentaacetyl-$\beta$-D-glucopyranose and 58.1 g (0.15 mole) of cholesterol. The mixture was heated to obtain a melt. After addition of 0.7 g of 12silicomolybdic acid to the melt, the mixture was refluxed in an atmospheric pressure for 5 hours. The reaction mixture was cooled to room temperature after which 200 ml of chloroform was added thereto. The mixture was washed with 2 portions of 100 ml of 4% $NaHCO_3$ aqueous solution and with 2 portions of 100 ml of water. The chloroform layer was dried over anhydrous magnesium sulfate.

The magnesium sulfate was filtered off and the filtrate was concentrated under reduced pressure, giving 68 g of pale yellow solid. The solid was purified by silica gel column chromatography using as an eluent hexane-ethyl acetate (5 : 1), producing 21.2 g of the desired compound, cholesteryl 2,3,4,6-tetra-O-acetyl-$\beta$-D-glucopyranoside in a yield of 59%.

COMPARISON EXAMPLE 17

The same reaction as in Example 19 was repeated with the exception of using p-toluenesulfonic acid as a catalyst. The resulting reaction mixture was subjected to a thin layer chromatography but the spot of cholesteryl 2,3,4,6-tetra-O-acetyl-D-glucopyranoside was not detected.

We claim:

1. A process for preparing a glycoside derivative by conversion of a saccharide compound to a glycoside derivative, characterized in that the reaction for conversion to glycoside is conducted in the presence of a catalyst comprising at least one of the heteropoly acids represented by the formula $$H_aX_pM_qO_r \cdot bH_2O$$

wherein X is P, As, Si or Ge, M is at least one species selected from the group consisting of Mo, W and V, a is 3 4 or 6, b is an integer of 0 to 30, p is 1 or 2, q is 12 or 18, and r is 40 or 62, with the proviso that when x is P or As, a is 3 or 6; when X is Si or Ge, a is 4; and further (1) when X is P or As and a is 3, or when X is Si or Ge and a is 4, M is at least one species selected from the group consisting of Mo, W and V, p is 1, q is 12 and r is 40; and (2) when X is P or As and a is 6, M is Mo or W, p is 2, q is 18 and r is 62.

2. A process for preparing a glycoside derivative in accordance with claim 1 in which said catalyst is selected from the group consisting of a heteropoly acid of Keggin structure represented by the formula $$H_{a'}XM_{12}O_{40} \cdot bH_2O$$

wherein X is P, As, Si or Ge, M is at least one species selected from the group consisting of Mo, W and V, a' is 3 or 4, with the provisio that when X is P or As, a' is 3 and when X is Si or Ge, a' is 4 and b is an integer of 0 to 30, and a heteropoly acid of Dawson structure represented by the formula $$H_6X'_2M'_{18}O_{62} \cdot bH_2O$$

wherein X' is P or As, M' is Mo or W and b is an integer of 0 to 30.

3. A process according to claim 1 which is characterized in that a metal salt is used in combination with the heteropoly acid.

4. A process according to claim 3 in which the metal salt is an inorganic acid salt or an organic acid salt of a metal pertaining to the Group II, IV or VIII of the periodic table or alkali metal.

5. A process according to claim 4 in which the metal salt is an acetate or sulfate of Cs, Co, Ni, Zn, Sn or Sr or a carbonate of Li, K or Na.

6. A process according to claim 3 in which the amount of the metal salt is about 2 to about 50% by weight based on the heteropoly acid.

7. A process according to claim 1 in which the reaction for conversion to glycoside derivative is a reaction comprising reacting an acylated saccharide with a saccharide having one or more unprotected OH groups or a compound represented by the formula $$R_1-AH$$

wherein $R_1$ is hydrocarbon group optionally having at least one substituent and A is oxygen atom or sulfur atom to produce a glycoside derivative having $R_1$-A- group, wherein $R_1$ and A are as defined above, introduced at 1-position of the saccharide.

8. A process according to claim 1 in which the the reaction for conversion to glycoside derivative is an aglycone exchange reaction comprising reacting an O-glycoside with an alcohol or a phenol both represented by the formula $$R_1-OH$$

wherein $R_1$ is hydrocarbon group optionally having at least one substitutent, to produce a glycoside derivative having $R_1$-O- group, wherein $R_1$ is as defined above, introduced at 1-position of the O-glycoside.

* * * * *